United States Patent
De Cointet et al.

(10) Patent No.: US 7,288,659 B2
(45) Date of Patent: Oct. 30, 2007

(54) ACYLAMINOTHIAZOLE DERIVATIVES, THEIR PREPARATION AND THERAPEUTIC USE

(75) Inventors: Paul De Cointet, Toulouse (FR); Pierre Despeyroux, Labarthe sur Leze (FR); Daniel Frehel, Estadens (FR); Chantal Guenet, Pfettisheim (FR); Corinne Heckel, La Walck (FR); Jean-Pierre Maffrand, Portet sur Garonne (FR); Rebecca Pruss, Strasbourg (FR)

(73) Assignee: Sanofi-Aventis, Paris (FR)

( * ) Notice: Subject to any disclaimer, the term of this patent is extended or adjusted under 35 U.S.C. 154(b) by 542 days.

(21) Appl. No.: 10/485,837

(22) PCT Filed: Aug. 5, 2002

(86) PCT No.: PCT/FR02/02802

§ 371 (c)(1),
(2), (4) Date: Feb. 4, 2004

(87) PCT Pub. No.: WO03/014095

PCT Pub. Date: Feb. 20, 2003

(65) Prior Publication Data

US 2004/0171643 A1 Sep. 2, 2004

(30) Foreign Application Priority Data

Aug. 6, 2001 (FR) .................................... 01 10504
Jun. 12, 2002 (FR) .................................... 02 07222

(51) Int. Cl.
*C07D 277/46* (2006.01)
(52) U.S. Cl. .................................... 548/195
(58) Field of Classification Search ................ 548/195
See application file for complete search history.

(56) References Cited

FOREIGN PATENT DOCUMENTS

| WO | WO 98/22433 | 5/1998 |
|---|---|---|
| WO | WO 98/22494 | 5/1998 |
| WO | WO 98/28268 | 7/1998 |
| WO | WO 98/38177 | 9/1998 |
| WO | WO 00/19210 | 4/2000 |
| WO | WO 00/24392 | 5/2000 |

OTHER PUBLICATIONS

Pallàs et al., Current Pharmaceutical Design, (2006), 12(33), pp. 4389-4408.*
Chemical Abstracts, 132:322142 (2000).

* cited by examiner

*Primary Examiner*—Laura L. Stockton
(74) *Attorney, Agent, or Firm*—Balaram Gupta

(57) ABSTRACT

The invention concerns a compound of general formula (I), wherein: X represents an oxygen or sulphur atom; $R_1$ represents, independently of each other when n=2 or 3, a halogen atom, a hydroxy, a $C_1$-$C_3$ alkyl, a $C_1$-$C_3$ alkoxy, a trifluoromethyl, a trifluoromethyloxy or a methylenedioxy; $R_2$ represents a $C_1$-$C_6$ alkyl group optionally substituted, a $C_3$-$C_7$ cycloalkyl, piperidinyl or phenyl group, the $C_3$-$C_7$ cycloalkyl, piperidinyl or phenyl groups being optionally substituted; $R_3$ represents a hydrogen atom or a $C_1$-$C_6$ alkyl group optionally substituted; $R_4$ represents a hydrogen atom or a $C_1$-$C_4$ alkyl group; and $R_5$ and $R_{5'}$ represent, independently of each other, a hydrogen atom, a hydroxy, a halogen atom, a $C_1$-$C_3$ alkyl group, or $R_5$ and $R_{5'}$ form together an oxo group; $R_6$ represents a hydrogen atom, a halogen atom, a $C_1$-$C_3$ alkyl, a $C_1$-$C_3$ alkoxy, a trifluoromethyl, or a trifluoromethoxy; in the form of a base, addition to an acid, hydrate or solvate. The invention is applicable in therapy (I)

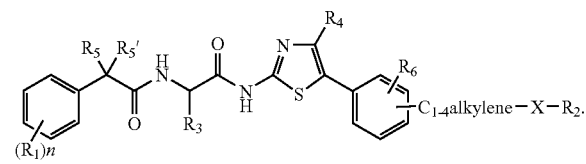

12 Claims, No Drawings

ACYLAMINOTHIAZOLE DERIVATIVES, THEIR PREPARATION AND THERAPEUTIC USE

The subject of the invention is acylaminothiazole derivatives, their preparation and their therapeutic use.

The first subject of the present invention is compounds corresponding to the general formula (I):

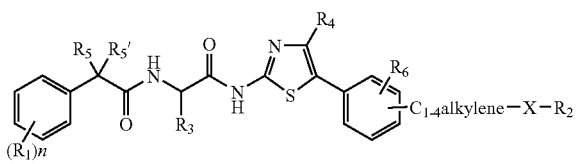

in which, n is equal to 0, 1, 2 or 3;

X represents an oxygen or sulfur atom;

$R_1$ represents, independently of each other when n=2 or 3, a halogen atom, a hydroxyl, a $C_{1-3}$ alkyl, a $C_{1-3}$ alkoxy, a trifluoromethyl, a trifluoromethyloxy or a methylenedioxy;

$R_2$ represents a $C_{1-6}$ alkyl group optionally substituted with a $C_{3-7}$ cycloalkyl group, a phenyl, a $C_{1-3}$ alkoxy group, a hydroxyl or a halogen atom; a $C_{3-7}$ cycloalkyl, piperidinyl or phenyl group;

the $C_{3-7}$ cycloalkyl, piperidinyl and phenyl groups being optionally substituted with one or more $C_{1-3}$ alkyl groups, $C_{1-3}$ alkoxy groups, a hydroxyl or a halogen atom;

$R_3$ represents a hydrogen atom or a $C_{1-6}$ alkyl group optionally substituted with a $C_{3-7}$ cycloalkyl group;

$R_4$ represents a hydrogen atom or a $C_{1-4}$ alkyl group;

$R_5$ and $R_{5'}$ represent, independently of each other, a hydrogen atom, a hydroxyl, a halogen atom, a $C_{1-3}$ alkyl group; or $R_5$ and $R_{5'}$ form together an oxo group; and $R_6$ represents a hydrogen atom, a halogen atom, a $C_{1-3}$ alkyl, a $C_{1-3}$ alkoxy, a trifluoromethyl or a trifluoromethoxy.

Among the compounds of general formula (I), the preferred compounds are those for which:

X represents an oxygen or sulfur atom; and/or $R_1$ represents, independently of each other when n=2 or 3, a halogen atom, a methylenedioxy, a $C_{1-3}$ alkyl group, a $C_{1-3}$ alkoxy group or a trifluoromethyloxy; more particularly a halogen atom; and/or $R_2$ represents a $C_{1-4}$ alkyl group optionally substituted with a $C_{4-7}$ cycloalkyl or phenyl group; a $C_{4-7}$ cycloalkyl, piperidinyl or phenyl group; the $C_{4-7}$ cycloalkyl, piperidinyl and phenyl groups being optionally substituted with one or more groups, preferably with 1 or 2 groups, $C_{1-3}$ alkyl or $C_{1-3}$ alkoxy; and/or $R_3$ represents a hydrogen atom or a $C_{1-4}$ alkyl group, more particularly a methyl, ethyl, propyl, optionally substituted with a $C_{4-7}$ cycloalkyl group; and/or $R_4$ represents a hydrogen atom or a $C_{1-3}$ alkyl group, more particularly methyl; and/or $R_5$ and $R_{5'}$ represent, independently of each other, a hydrogen or halogen atom and more particularly a fluorine atom, a hydroxyl or a $C_{1-3}$ alkyl group and more particularly a methyl; or $R_5$ and $R_{5'}$ form together an oxo group; and/or $R_6$ is a hydrogen atom or a $C_{1-3}$ alkoxy and more particularly a methoxy.

The compounds for which X, $R_1$, $R_2$, $R_3$, $R_4$, $R_5$, $R_{5'}$ and $R_6$ are all as defined above in the subgroups of preferred compounds are particularly preferred and more specifically among these the compounds for which:

X represents an oxygen atom; and/or $R_1$ represents a fluorine atom at the 3-position and another fluorine atom at the 5-position (n=2).

By way of example of preferred compounds, the following compounds may be mentioned:

1: (2S)-2-{[2-(3,5-difluorophenyl)acetyl]amino}-N-{5-[2-(isopropoxymethyl)phenyl]-1,3-thiazol-2-yl}propanamide 2: N-(5-{2-[(cyclohexyloxy)methyl]phenyl}-1,3-thiazol-2-yl)-2-{[2-(3,5-difluorophenyl)acetyl]amino}propanamide 3: 2-{[2-(3,5-difluorophenyl)acetyl]amino}-N-{5-[2-(ethoxymethyl)phenyl]-1,3-thiazol-2-yl}propanamide 4: 2-{[2-(3,5-difluorophenyl)acetyl]amino}-N-{5-[2-(isobutoxymethyl)phenyl]-1,3-thiazol-2-yl}propanamide 5: 2-{[2-(3,5-difluorophenyl)acetyl]amino}-N-{5-[2-(phenoxymethyl)phenyl]-1,3-thiazol-2-yl}propanamide 6: N-(5-{2-[(benzyloxy)methyl]phenyl}-1,3-thiazol-2-yl)-2-{[2-(3,5-difluorophenyl)acetyl]amino}propanamide 7: N-(5-{2-(cyclopentyloxy)methyl]phenyl}-1,3-thiazol-2-yl)-2-{[2-(3,5-difluorophenyl)acetyl]amino}propanamide 8: N-(5-{2-[(cyclohexylmethoxy)methyl]phenyl}-1,3-thiazol-2-yl)-2-{[2-(3,5-difluorophenyl)acetyl]amino}-propanamide 9: N-(5-{2-[(cyclohexyloxy)methyl]phenyl}-1,3-thiazol-2-yl)-2-{[2-(3,5-difluorophenyl)acetyl]amino}butanamide 10: N-(5-{2-[(cyclohexyloxy)methyl]phenyl}-1,3-thiazol-2-yl)-2-{[2-(3,5-difluorophenyl)acetyl]amino}-3-methylbutanamide 11: N-(5-{2-[(cyclohexyloxy)methyl]phenyl}-1,3-thiazol-2-yl)-2-[(2-phenylacetyl)amino]propanamide 12: N-(5-{2-[(cyclohexyloxy)methyl]phenyl}-4-methyl-1,3-thiazol-2-yl)-2-{[2-(3,5-difluorophenyl)acetyl]-amino}propanamide 13: 2-{[2-(3,5-difluorophenyl)acetyl]amino}-N-{5-[2-(methoxymethyl)phenyl]-1,3-thiazol-2-yl}propanamide 14: N-(5-{2-[(cyclopentyloxy)methyl]phenyl}-4-methyl-1,3-thiazol-2-yl)-2-{[2-(3,5-difluorophenyl)acetyl]-amino}propanamide 15: N-{2-[(5-{2-[(cyclohexyloxy)methyl]phenyl}-1,3-thiazol-2-yl)amino]-2-oxoethyl}-2-(3,5-difluorophenyl)-acetamide 16: (2S)-N-(5-{2-[(cyclohexyloxy)methyl]phenyl}-1,3-thiazol-2-yl)-2-{[2-(3-methylphenyl)acetyl]amino}-propanamide 17: (2S)-N-(5-{2-[(cyclohexyloxy)methyl]phenyl}-1,3-thiazol-2-yl)-2-{[2-(4-methylphenyl)acetyl]amino}-propanamide 18: (2S)-2-{[2-(3-chlorophenyl)acetyl]amino}-N-{5-{2-[(cyclohexyloxy)methyl]phenyl}-1,3-thiazol-2-yl}propanamide 19: (2S)-N-(5-{2-[(cyclohexyloxy)methyl]phenyl}-1,3-thiazol-2-yl)-2-{[2-(3-fluorophenyl)acetyl]amino}-propanamide 20: (2S)-N-(5-{2-[(cyclohexyloxy)methyl]phenyl}-1,3-thiazol-2-yl)-2-{[2-(4-fluorophenyl)acetyl]amino}-propanamide 21: (2S)-2-{[2-(3,5-difluorophenyl)acetyl]amino}-N-{5-[2-(phenoxymethyl)phenyl]-1,3-thiazol-2-yl}propanamide 22: (2S)-2-{[2-(3,5-difluorophenyl)acetyl]amino}-N-{5-[2-(isopropoxymethyl)phenyl]-1,3-thiazol-2-yl}propanamide 23: (2S)-N-(5-{2-[(cyclohexyloxy)methyl]phenyl}-4-methyl-1,3-thiazol-2-yl)-2-{[2-(3,5-difluorophenyl)-acetyl]amino}propanamide
24: (2S)-N-(5-{3-[(cyclohexyloxy)methyl]phenyl}-1,3-thiazol-2-yl)-2-{[2-(3,5-difluorophenyl)acetyl]amino}-propanamide
25: (2R)-N-(5-{2-[(cyclohexyloxy)methyl]phenyl}-1,3-thiazol-2-yl)-2-{[2-(3,5-difluorophenyl)acetyl]amino}-propanamide
26: (2S)-N-(5-{2-[(cyclohexyloxy)methyl]phenyl}-1,3-thiazol-2-yl)-2-{[2-(3,5-difluorophenyl)acetyl]amino}-propanamide
27: (2S)-2-{[2-(3,5-difluorophenyl)acetyl]amino}-N-{5-[2-(isopropoxymethyl)phenyl]-4-methyl-1,3-thiazol-2-yl}propanamide
28: (2S)-N-(5-{2-[(cyclopentyloxy)methyl]phenyl}-4-methyl-1,3-thiazol-2-yl)-2-{[2-(3,5-difluorophenyl)-acetyl]amino}propanamide
29: (2S)-2-{[2-(1,3-benzodioxol-5-yl)acetyl]amino}-N-(5-{2-[(cyclohexyloxy)methyl]phenyl}-1,3-thiazol-2-yl}propanamide
30: (2S)-N-(5-{2-[(cyclohexyloxy)methyl]phenyl}-1,3-thiazol-2-yl)-2-{[2-(3,4-difluorophenyl)acetyl]amino}-propanamide
31: (2S)-N-(5-{2-[(cyclohexyloxy)methyl]phenyl}-1,3-thiazol-2-yl)-2-{[2-(3,5-difluorophenyl)acetyl]amino}-3-methylbutanamide
32: (2S)-N-(5-{2-[(cyclohexyloxy)methyl]phenyl}-1,3-thiazol-2-yl)-2-{[2-(3,5-difluorophenyl)acetyl]amino}-butanamide
33: (2S)-N-(5-{2-[(cyclohexyloxy)methyl]phenyl}-1,3-thiazol-2-yl)-2-{[2-(4-methoxyphenyl)acetyl]amino}-propanamide
34: (2S)-N-(5-{2-[(cyclohexyloxy)methyl]phenyl}-1,3-thiazol-2-yl)-2-{[2-(3-methoxyphenyl)acetyl]amino}-propanamide
35: (2S)-N-(5-{2-[(cyclohexyloxy)methyl]phenyl}-1,3-thiazol-2-yl)-2-{[2-(3,5-dimethoxyphenyl)acetyl]amino}-propanamide
36: (2S)-N-(5-{2-[(cyclohexyloxy)methyl]phenyl}-1,3-thiazol-2-yl)-2-{[2-(3,5-difluorophenyl)acetyl]amino}-4-methylpentanamide
37: (2S)-N-(5-{2-[(cyclohexyloxy)methyl]phenyl}-1,3-thiazol-2-yl)-2-{[2-(3,5-difluorophenyl)acetyl]amino}-3,3-dimethylbutanamide
38: (2S)-2-{[2-(4-chlorophenyl)acetyl]amino}-N-(5-{2-[(cyclohexyloxy)methyl]phenyl}-1,3-thiazol-2-ylpropanamide
39: (2S)-N-(5-{4-[(cyclohexyloxy)methyl]phenyl}-1,3-thiazol-2-yl)-2-{[2-(3,5-difluorophenyl)acetyl]amino}-propanamide
40: (2S)-2-{[2-(3,5-difluorophenyl)acetyl]amino}-N-{5-[2-isobutoxymethyl)phenyl]-1,3-thiazol-2-yl}propanamide
41: (2S)-2-{[2-(3,5-difluorophenyl)acetyl]amino)-N-(5-[2-(ethoxymethyl)phenyl]-1,3-thiazol-2-yl}propanamide
42: (2S)-N-(5-{2-[(cyclohexyloxy)methyl]phenyl}-1,3-thiazol-2-yl)-2-{[2-(3,5-difluorophenyl)acetyl]amino}-pentanamide
43: (2S)-N-(5-{3-[(cyclohexylmethoxy)methyl]phenyl}-1,3-thiazol-2-yl)-2-{[2-(3,5-difluorophenyl)acetyl]amino}propanamide
44: (2S)-3-cyclohexyl-N-(5-{2-[(cyclohexyloxy)methyl]phenyl}-1,3-thiazol-2-yl)-2-{[2-(3,5-difluorophenyl)-acetyl]amino}propanamide
45: (2S)-2-{[2-(3,5-difluorophenyl)acetyl]amino}-N-(5-{3-(isopropoxymethyl)phenyl}-1,3-thiazol-2-yl)propanamide
46: (2S)-N-(5-{4-[(cyclohexylmethoxy)methyl]phenyl}-1,3-thiazol-2-yl)-2-{[2-(3,5-difluorophenyl)acetyl]-amino}propanamide
47: (2S)-N-(5-{2-[(cyclohexyloxy)methyl]phenyl}-1,3-thiazol-2-yl)-2-{[2-(3,5-difluorophenyl)acetyl]amino}-hexanamide
48: (2S)-N-(5-{2-[(cyclohexyloxy)methyl]phenyl}-1,3-thiazol-2-yl)-2-{[2-(3-trifluoromethoxyphenyl)acetyl]-amino}propanamide
49: (2S)-N-(5-{2-[(cyclopentyloxy)methyl]phenyl}-1,3-thiazol-2-yl)-2-{[2-(3,5-difluorophenyl)acetyl]amino}-propanamide
50: (2S)-N-(5-{2-[(cyclohexyloxy)methyl]phenyl}-1,3-thiazol-2-yl)-2-{[(2R)-2-(3,5-difluorophenyl)-2-hydroxy-acetyl]amino}propanamide
51: (2S)-N-(5-{2-[(cyclohexyloxy)methyl]phenyl}-1,3-thiazol-2-yl)-2-{[(2S)-2-(3,5-difluorophenyl)-2-hydroxy-acetyl]amino}propanamide
52: (2S)-N-(5-{2-[(cyclohexyloxy)methyl]phenyl}-4-methyl-1,3-thiazol-2-yl)-2-{[2-(3,5-difluorophenyl)-acetyl]amino}pentanamide
53: (2S)-N-(5-{2-[(cyclohexyloxy)methyl]phenyl}-4-methyl-1,3-thiazol-2-yl)-2-{[(2R)-2-(3,5-difluorophenyl)-2-hydroxyacetyl]amino}pentanamide
54: (2S)-N-(5-{2-[(cyclohexylsulfanyl)methyl]phenyl}-1,3-thiazol-2-yl)-2-{[2-(3,5-difluorophenyl)acetyl]-amino}propanamide
55: (2S)-N-(5-{2-[(cyclohexyloxy)methyl]phenyl}-1,3-thiazol-2-yl)-2-{[(2S)-2-(3,5-difluorophenyl)-2-hydroxy-acetyl]amino}pentanamide
56: (2S)-N-(5-{2-[(cyclohexyloxy)methyl]phenyl}-1,3-thiazol-2-yl)-2-{[(2R)-2-(3,5-difluorophenyl)-2-hydroxy-acetyl]amino}pentanamide
57: (2S)-N-(5-{2-[(cyclohexyloxy)methyl]phenyl}-4-methyl-1,3-thiazol-2-yl)-2-{[(2S)-2-(3,5-difluorophenyl)-2-hydroxyacetyl]amino}pentanamide
58: (2S)-N-(5-{2-[(cyclohexyloxy)methyl]phenyl}-1,3-thiazol-2-yl)-2-{[2-(3,5-difluorophenyl)propanoyl]-amino}pentanamide
59: (2S)-N-(5-{2-[(cyclohexyloxy)methyl]phenyl}-4-ethyl-1,3-thiazol-2-yl)-2-{[2-(3,5-difluorophenyl)-acetyl]amino}pentanamide
60: (2S)-N-(5-{2-[(cyclohexyloxy)methyl]phenyl}-1,3-thiazol-2-yl)-2-{[2-(3,5-difluorophenyl)-2-oxoacetyl]-amino}pentanamide
61: (2S)-N-(5-{2-[(cyclohexyloxy)methyl]phenyl}-1,3-thiazol-2-yl)-2-{[2-(3,5-difluorophenyl)-2-oxoacetyl]-amino}propanamide
62: (2S)-N-(5-{2-[(cyclohexyloxy)methyl]phenyl}-4-ethyl-1,3-thiazol-2-yl)-2-{[2-(3,5-difluorophenyl)-acetyl]amino}propanamide
63: (2S)-N-(5-{2-[(cyclohexyloxy)methyl]phenyl}-4-isopropyl-1,3-thiazol-2-yl)-2-{[2-(3,5-difluorophenyl)-acetyl]amino}pentanamide
64: (2S)-N-(5-{2-[(cyclohexyloxy)methyl]phenyl}-1,3-thiazol-2-yl)-2-{[2-(3,5-difluorophenyl)-2-fluoroacetyl]-amino}pentanamide
65: (2S)-N-(5-{2-[(cyclohexyloxy)methyl]phenyl}-1,3-thiazol-2-yl)-2-{[(2R)-2-(3,5-difluorophenyl)-2-fluoro-acetyl]amino}propanamide.
66: (2S)-N-(5-{2-[(cyclohexyloxy)methyl]phenyl}-1,3-thiazol-2-yl)-2-{[(2S)-2-(3,5-difluorophenyl)-2-fluoro-acetyl]amino}propanamide
67: (2S)-N-(5-{2-[(cyclohexyloxy)methyl]phenyl}-1,3-thiazol-2-yl)-2-{[2-(3,5-difluorophenyl)-2-fluoroacetyl]-amino}pentanamide 68: (2S)-N-(5-{2-[(N-methylpiperidin-4-yloxy)methyl]-phenyl}-4-methyl-1,3-thiazol-2-yl)-2-{[2-(3,5-difluorophenyl)acetyl]amino}pentanamide
69: (2S)-2-{[2-(3,5-difluorophenyl)acetyl]amino}-N-{5-[2-(isopropoxymethyl)phenyl]-4-methyl-1,3-thiazol-2-yl}butanamide
70: (2S)-2-{[2-(3,5-difluorophenyl)acetyl]amino}-N-{5-[2-(isopropoxymethyl)phenyl]-1,3-thiazol-2-yl}butanamide
71: (2S)-2-{[2-(3,5-difluorophenyl)acetyl]amino}-N-{5-[2-(isopropoxymethyl)phenyl]-4-methyl-1,3-thiazol-2-yl}pentanamide
72: (2S)-2-{[2-(3,5-difluorophenyl)acetyl]amino}-N-{5-[2-(isopropoxymethyl)phenyl]-1,3-thiazol-2-yl}pentanamide
73: (2S)-2-{[2-(3,5-difluorophenyl)acetyl]amino}-N-[5-(2-{[(4-methoxycyclohexyl)oxy]methyl}phenyl]-1,3-thiazol-2-yl}propanamide
74: (2S)-N-(5-{2-[(cyclohexyloxy)methyl]phenyl}-1,3-thiazol-2-yl)-2-{[2-(3,5-difluorophenyl)-2,2-difluoroacetyl]amino}pentanamide
75: (2S)-2-{[2-(3,5-difluorophenyl)acetyl]amino}-N-(5-{2-(isopropoxymethyl)-4-methoxyphenyl}-1,3-thiazol-2-yl)pentanamide In the context of the invention, the expression:

$C_{t-z}$ where t and z may take the values from 1 to 7, is understood to mean a carbon chain which may have from t to z carbon atoms, for example $C_{1-3}$ a carbon chain which may have from 1 to 3 carbon atoms, $C_{3-6}$ a carbon chain which may have from 3 to 6 carbon atoms; and the like;

alkyl is understood to mean a linear or branched saturated aliphatic group, for example a $C_{1-6}$ alkyl group represents a linear or branched carbon chain of from 1 to 6 carbon atoms, more particularly a methyl, ethyl, propyl, isopropyl, butyl, isobutyl, sec-butyl, tert-butyl, and the like, preferably a methyl, ethyl, propyl or isopropyl;

alkylene is understood to mean a divalent alkyl group;

cycloalkyl is understood to mean a cyclic alkyl group, for example a $C_{3-7}$ cycloalkyl group represents a cyclic carbon chain of from 3 to 7 carbon atoms, more particularly a cyclopropyl, cyclobutyl, cyclopentyl, cyclohexyl, cycloheptyl, preferably a cyclopentyl or cyclohexyl;

alkoxy is understood to mean an alkyloxy group having a linear or branched saturated aliphatic chain;

halogen atom is understood to mean a fluorine, a chlorine, a bromine or an iodine; and "$R_5$ and $R_{5'}$ form together an oxo group" is understood to mean the group such that:

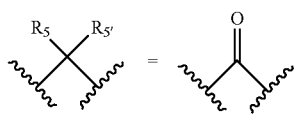

The compounds of general formula (I) may contain one or more asymmetric carbons. They may therefore exist in the form of enantiomers or of diastereoisomers. These enantiomers or diastereoisomers, and mixtures thereof, including the racemic mixtures, form part of the invention.

The compounds of formula (I) may exist in the form of bases or of addition salts with acids. Such addition salts form part of the invention. These salts are advantageously prepared with pharmaceutically acceptable acids, but the salts of other useful acids, for example, for the purification or the isolation of the compounds of formula (I), also form part of the invention.

The compounds of general formula (I) may exist in the form of hydrates or of solvates, namely in the form of associations or combinations with one or more molecules of water or with a solvent. Such hydrates and solvates also form part of the invention.

In the text which follows, the expression leaving group is understood to mean a group which can be easily cleaved from a molecule, with departure of an electron pair, by the breaking of a heterolytic bond. This group may thus be easily replaced by another group during a substitution reaction for example. Such leaving groups are, for example, halogens, or an activated hydroxyl group such as a mesylate, tosylate, triflate, acetyl and the like. Examples of leaving groups and references for their preparation are given in "Advanced Organic Chemistry", J. March, $3^{rd}$ Edition, Wiley Interscience, p. 310-316.

The expression protecting group is understood to mean a group which makes it possible to prevent the reactivity of a functional group or a position, during a chemical reaction which may affect it, and which releases the molecule after cleavage according to methods known to persons skilled in the art. Examples of protecting groups and methods of protection and deprotection are given, inter alia, in *Protective groups in Organic Synthesis*, Greene et al., $2^{nd}$ Ed. (John Wiley & Sons, Inc., New York).

The second subject of the present invention is methods for preparing the compounds of formula (I).

Thus, these compounds may be prepared by methods, illustrated in the schemes which follow, whose operating conditions are conventional for persons skilled in the art.

According to Scheme 1, the compound of formula (I) may be obtained by peptide coupling of the 2-aminothiazole of formula (VII) with the acylamino acid of formula (VIII) according to conditions known to persons skilled in the art, for example in the presence of benzotriazol-1-yloxy-tris (dimethylamino)phosphonium hexafluorophosphate (BOP) and N-ethylmorpholine or N-methylmorpholine in an inert solvent such as dimethylformamide, acetonitrile or dichloromethane at a temperature which may range from 0° C. to room temperature.

The compound of formula (VIII) is obtained by prior saponification of the compound of formula (IX) according to methods known to persons skilled in the art.

Scheme 1

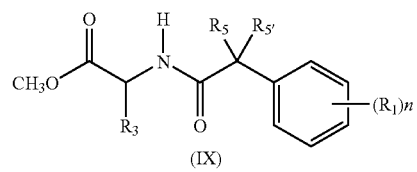

(IX)

↓ Saponification

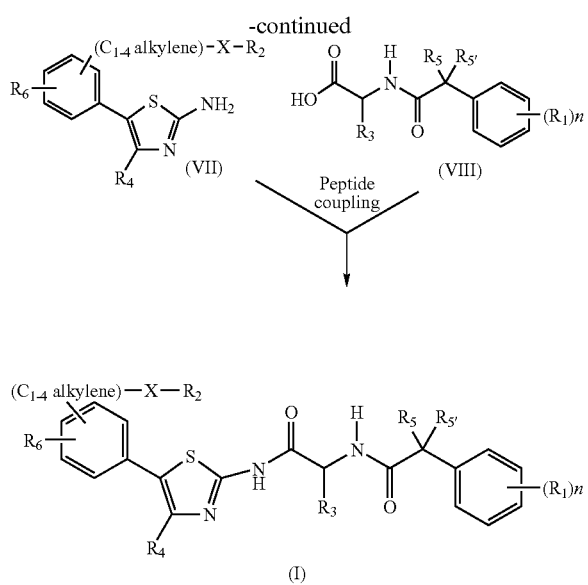

The compounds of formula (VII) may be prepared according to Scheme 2.

According to this scheme, the aralkyls of formula (X), in which Y represents a leaving group, preferably a halogen atom such as bromine and Z represents a halogen atom such as bromine, are condensed with alkali metal thiolates or alcoholates, for example of formula $R_2X^- Na^+$ in which X represents an oxygen or sulfur atom. The reaction is carried out in an inert solvent such as dimethylformamide at a temperature which may range from 0° C. to 50° C., to give the compounds of formula (II). The aryl of formula (II) is converted to boronic acid of formula (III) according to an adaptation of the method described by Schoevaars, J. Am. Chem. Soc., 1999, 121, 9550-9561. The conversion may, for example, be carried out by prior formation of the anion of the compound of formula (II), for example by the action of a strong base such as butyllithium, in an ethereal solvent such as tetrahydrofuran, at temperatures which may range from −50° C. to −80° C. This anion is then reacted with a borate such as trimethyl borate to give, after hydrolysis, the boronic acid of formula (III).

The coupling of the boronic acid (III) with the thiazole of formula (V) in which Pg represents a protecting group, such as an imino, for example more particularly a diphenyl ketone imine, may be carried out according to the Suzuki reaction, by adaptation of the method described by Wolfe, J. Org. Chem., 1997, 62, 4943-4948, to give the 5-phenylthiazole of formula (VI). The coupling is carried out, for example, in an ethereal solvent such as dioxane in the presence of tripotassium phosphate trihydrate and a catalyst such as tetrakis (triphenylphosphine)palladium (0) at a temperature which may range from room temperature to the reflux temperature of the solvent. The 5-phenylthiazole of formula (VI) thus prepared is then deprotected according to methods known to persons skilled in the art to generate the 5-phenyl-2-aminothiazole of formula (VII).

Scheme 2

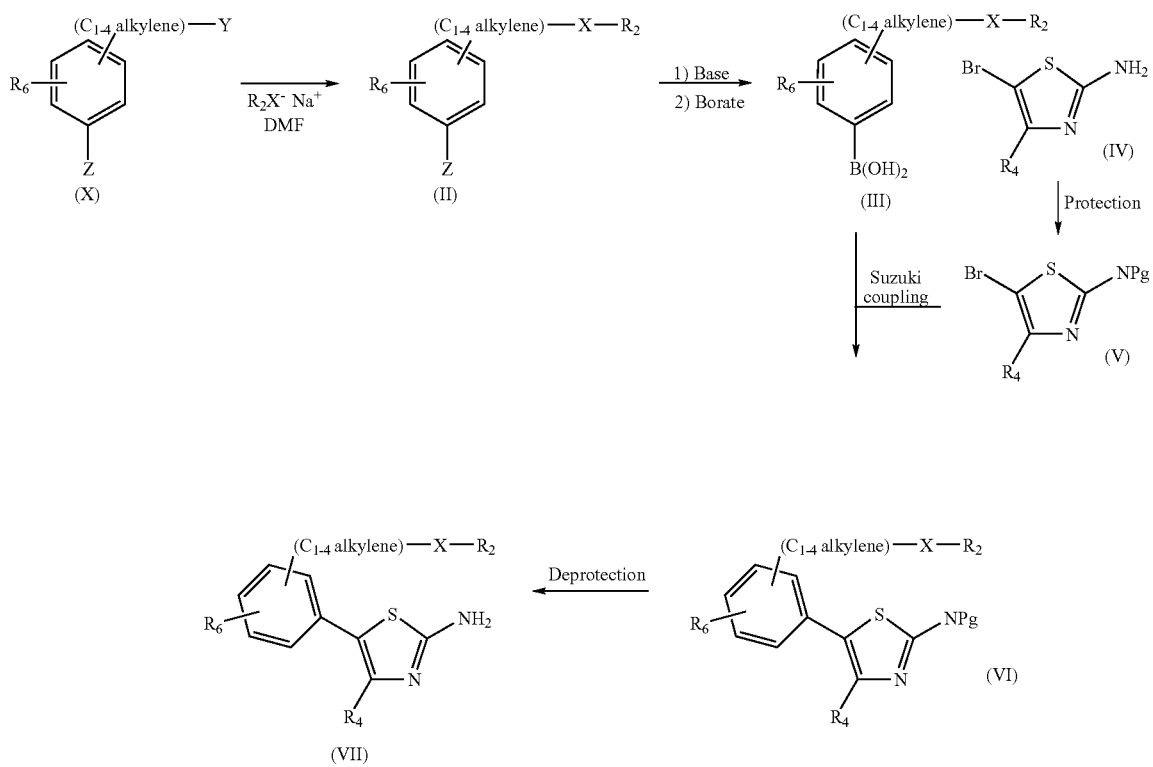

The 5-bromothiazole of formula (V) is obtained by protecting the amino functional group of the corresponding compound of formula (IV). Preferably, it is protected in the form of a diphenyl ketone imine under conditions known to persons skilled in the art.

Alternatively, the optically active compounds of formula (I), in which $R_3$ is not a hydrogen, may be obtained according to Scheme 3 by stereospecific synthesis.

According to this scheme, the compound of formula (I) may be obtained by peptide coupling of the amine of formula (XIII) with the acid of formula (XIV) according to conditions known to persons skilled in the art, for example in the presence of benzotriazol-1-yloxy-tris(dimethylamino) phosphonium hexafluorophosphate (BOP) and N-ethylmorpholine or N-methylmorpholine in an inert solvent such as dimethylformamide, acetonitrile or dichloromethane at a temperature which may range from 0° C. to room temperature.

The amine of formula (XIII) is obtained by peptide coupling of the amine of formula (VII) with the amino acid of formula (XI), in which Pg represents a protecting group, under conditions as described above, to give the compound of formula (XII). The amino acid of formula (XI) is, for example, protected by means of an N-tert-butyloxycarbonyl (Boc). The compound (XII) is then deprotected according to methods known to persons skilled in the art. For example, if the protecting group used is Boc, the latter may be deprotected by acid hydrolysis, in the presence of anhydrous gaseous hydrochloric acid.

The starting compounds, in particular the compounds of formula (IV), (IX), (X), (XI) and (XIV) are commercially available or are described in the literature, or may be prepared by methods which are described therein or which are known to persons skilled in the art.

For example, 5-bromo-2-aminothiazole (IV) may be obtained by bromination of the corresponding 2-aminothiazole according to an adaptation of the method described by Kaye, J. Chem. Soc. Perkins I, 1981, 2335-2339.

Scheme 3

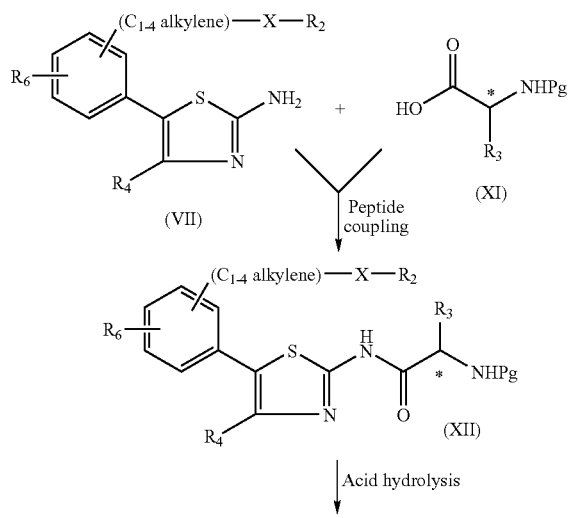

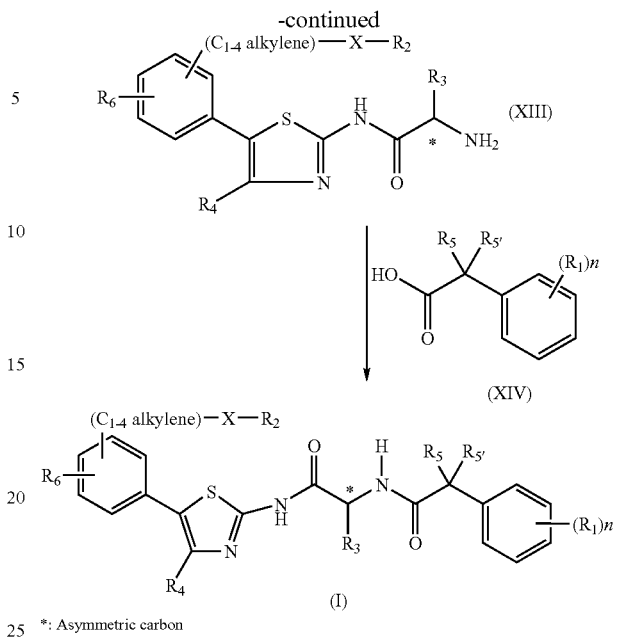

*: Asymmetric carbon

For example, the compound of formula (IX) may be obtained according to the methods described in patent applications WO 98/22430 and WO 98/22441.

For example, the compound of formula (XIV) may be obtained by adaptation of the methods described by Middleton et al., J. Org. Chem., 45, 14, 1980, 2883-2887 and by Miyamoto et al., J. Amer. Chem. Soc., 114, 15, 1992, 6256-6257.

When a functional group of a compound is reactive, for example when $R_1$ represents a hydroxyl, it may require prior protection before reaction. Persons skilled in the art will be able to easily determine the need for such prior protection.

The meanings of n, X, $R_1$, $R_2$, $R_3$, $R_4$, $R_5$, $R_{5'}$ and $R_6$ in the compounds of formula (II) to (XIV) are as defined for the compounds of formula (I).

The compounds of formula (VI), when —NPg represents a diphenylimine, of formula (VII) and of formula (XIII) are novel and also form part of the invention. They are useful as synthesis intermediates for the preparation of the compounds of general formula (I).

The following examples describe the preparation of some compounds in accordance with the invention. These examples are not limiting and only illustrate the invention.

The exemplified compound numbers refer to those given in the Table below. The elemental microanalyses and the NMR, IR or mass spectra confirm the structure of the compounds obtained.

EXAMPLE 1

(2S)-N-(5-{2-[(cyclohexyloxy)methyl]phenyl}-1,3-thiazol-2-yl)-2-{[2-(3,5-difluorophenyl)acetyl]-amino}propanamide (Compound No. 26)

EXAMPLE 1.1

1-bromo-2-[(cyclohexyloxy)-methyl]benzene 1.2 g of sodium hydride at 50% in suspension in oil are added at 5° C., in portions, to 5 g of cyclohexanol in solution in 150 ml of dimethylformamide. The mixture is stirred for 1 hour at room temperature and 12.5 g of 2-bromobenzyl bromide in solution in 15 ml of dimethylformamide are introduced at 5° C. After 2 hours at room temperature, the reaction medium is poured over ice-cold water and extracted with ethyl acetate. The organic phase is dried over anhydrous sodium sulfate and evaporated to give 13.3 g of oil.

$^1$H NMR: δ in ppm (DMSO d6): 1.2-1.95 (unresolved complex, 10H); 3.45 (m, 1H); 4.53 (s, 2H); 7.25 (t, 1H); 7.38 (t, 1H); 7.55 (d, 1H); 7.62 (d, 1H).

EXAMPLE 1.2

2-[(cyclohexyloxy)methyl]phenylboronic acid 31.2 ml of n-butyllithium (1.6 M) in solution in n-hexane are added dropwise at −70° C. to 13.45 g of 1-bromo-2-[(cyclohexyloxy)methyl]benzene, obtained in step 1.1, in solution in 150 ml of tetrahydrofuran. After 2 hours at −70° C., 10.2 ml of trimethyl borate are introduced dropwise and the temperature of the reaction medium is allowed to rise to −30° C. The medium is hydrolyzed with a saturated ammonium chloride solution, and then extracted with ethyl acetate and the organic phase is dried with anhydrous sodium sulfate. After evaporation, 11.7 g of a yellow oil are obtained.

$^1$H NMR: δ in ppm (DMSO d6): 1.15-1.95 (unresolved complex, 10H); 3.35 (m, 1H); 4.61 (s, 2H); 7.20-7.35 (unresolved complex, 3H); 7.52 (d, 1H); 8.00 (s, 2H).

EXAMPLE 1.3

5-bromo-N-(diphenylmethylene)-1,3-thiazol-2-amine 26 g of benzophenone imine are added to 34 g of 5-bromo-1,3-thiazol-2-amine hydrobromide, in suspension in 300 ml of 1,2-dichloroethane. The mixture is kept under reflux for 18 hours. The precipitate formed is filtered and the filtrate is concentrated to give 37.2 g of solid. m.p.=109° C.

$^1$H NMR: δ in ppm (DMSO d6): 7.34 (m, 2H); 7.50-7.76 (unresolved complex, 9H).

EXAMPLE 1.4

5-{2-[(cyclohexyloxy)methylphenyl}-N-(diphenylmethylene)-1,3-thiazol-2-amine 24 g of tripotassium phosphate trihydrate, 16.7 g of 2-[(cyclohexyloxy)methyl]phenylboronic acid, obtained in step 1.2, and 2 g of tetrakis(triphenylphosphine)palladium (0) are successively introduced into 17 g of 5-bromo-N-(diphenylmethylene)-1,3-thiazol-2-amine, obtained in step 1.3, in suspension in 250 ml of 1,4-dioxane, and the mixture is kept at 60° C. for 18 hours. The reaction medium is evaporated to dryness, the residue is taken up in ethyl acetate and washed with water. The organic phase is dried over anhydrous sodium sulfate and concentrated. The residue is chromatographed on a silica gel column, eluting with dichloromethane to give 37.2 g of a yellow oil.

$^1$H NMR: δ in ppm (DMSO d6): 1.30-1.95 (unresolved complex, 10H); 3.40 (m, 1H); 4.64 (s, 2H); 7.20-7.85 (unresolved complex, 15H).

EXAMPLE 1.5

5-{2-[(cyclohexyloxy)methyl]-phenyl}-1,3-thiazol-2-amine 75 ml of an aqueous hydrochloric acid solution (1 M) are added to 11 g of 5-{-2-[(cyclohexyloxy)methyl]phenyl}-N-(diphenylmethylene)-1,3-thiazol-2-amine, obtained in step 1.4, in solution in 150 ml of methanol, and the mixture is stirred for 18 hours at 20° C. The mixture is evaporated to dryness, the residue is taken up in diethyl ether and washed with an aqueous sodium hydroxide solution (0.5 M). The organic phase is dried over anhydrous sodium sulfate and concentrated. The residue is chromatographed on a silica gel column, eluting with a dichloromethane/methanol 98/2 (v/v) mixture, to give 5.3 g of a beige-colored solid. m.p.=102° C.

$^1$H NMR: δ in ppm (DMSO d6): 1.15-1.95 (unresolved complex, 10H); 3.40 (m, 1H); 4.51 (s, 2H); 7.05 (s, 2H); 7.08 (s, 1H); 7.25-7.40 (unresolved complex, 4H).

EXAMPLE 1.6 tert-butyl(1S)-2-[(5-{2-[(cyclohexyloxy)methyl]phenyl}-1,3-thiazol-2-yl)amino]-1-methyl-2-oxoethylcarbamate 9 g of benzotriazol-1-yloxytris(dimethylamino)phosphonium hexafluorophosphate are added at 0° C. to 4 g of (2S)-2-[(tert-butyloxycarbonyl)amino]-propionic acid in solution in 35 ml of dimethylformamide, followed dropwise by 5.5 ml of N-ethylmorpholine. After 15 minutes at this temperature, 3.7 g 5-{-2-[(cyclohexyloxy)methyl]phenyl}-1,3-thiazol-2-amine, obtained in step 1.5, in solution in 10 ml of dimethylformamide are introduced and the mixture is stirred for 18 hours at room temperature. The medium is taken up in ethyl acetate and washed twice with water. The organic phase is dried over anhydrous sodium sulfate and concentrated. The residue is chromatographed on a silica gel column, eluting with a dichloromethane/methanol 96/4 (v/v) mixture to give 5.4 g of a colorless oil.

$^1$H NMR: δ in ppm (DMSO d6): 1.16-1.49 (unresolved complex, 18H); 1.68-1.88 (unresolved complex, 4H); 3.36 (m, 1H); 4.27 (m, 1H); 4.49 (s, 2H); 7.25 (d, 1H); 7.37-7.61 (unresolved complex, 5H); 12.19 (s, 1H). $[α]_D^{20}$=−56.7 (c=1/CH$_3$OH).

EXAMPLE 1.7

(2S)-2-amino-N-(5-{2-[(cyclohexyloxy)methyl]phenyl}-1,3-thiazol-2-yl)propionamide hydrochloride 25 ml of a solution of gaseous hydrochloric acid (4.5 N) in diethyl ether are added dropwise at 0° C. to 4 g of tert-butyl (1S)-2-[(5-{2-[(cyclohexyloxy)-methyl]phenyl}-1,3-thiazol-2-yl)amino]-1-methyl-2-oxoethylcarbamate, obtained in step 1.6, in solution in 60 ml of ethyl acetate. The mixture is stirred for 18 hours at room temperature. The precipitate formed is filtered, rinsed twice with diethyl ether and dried to give 2.9 g of a white solid. m.p.=140° C.

$^1$H NMR: δ in ppm (DMSO d6): 1.19-1.48 (unresolved complex, 9H); 1.66-1.90 (unresolved complex, 4H); 3.37 (m, 1H); 4.18 (m, 1H); 4.50 (s, 2H); 7.37-7.57 (unresolved complex, 4H); 7.65 (s, 1H); 8.52 (s, 3H); 12.80 (s, 1H). $[α]_D^{20}$=+4.3 (c=1/CH$_3$OH).

EXAMPLE 1.8

(2S)-N-(5-{(2-[(cyclohexyloxy)-methyl]phenyl}-1,3-thiazol-2-yl)-2-{[2-(3,5-difluorophenyl)acetyl]amino}propanamide 0.884 g of benzotriazol-1-yloxy-tris(dimethylamine) phosphonium hexafluorophosphate and 0.5 ml of N-ethylmorpholine are added at 0° C. to 0.344 g of 3,5-difluorophenylacetic acid in solution in 10 ml of dimethylformamide, and the mixture is stirred for 15 minutes at this temperature. 0.65 g of (2S)-2-amino-N-(5-{2-[(cyclohexyloxy)methyl]phenyl}-1,3-thiazol-2-yl)propionamide hydrochloride, obtained in step 1.7, is introduced in portions, and the mixture is stirred for 18 hours at 20° C. The medium is taken up in ethyl acetate and washed twice with water. The organic phase is dried over anhydrous sodium sulfate and concentrated. The residue is chromatographed on a silica gel column, eluting with a dichloromethane/methanol 98/2 (v/v) mixture to give, after precipitation from water, 0.73 g of a white solid. m.p.=140° C.

$^1$H NMR: δ in ppm (DMSO d6): 1.15-1.36 (unresolved complex, 8H); 1.46 (m, 1H); 1.64-1.86 (unresolved complex, 4H); 3.35 (m, 1H); 3.56 (s, 2H); 4.47 (s, 2H); 4.52 (m, 1H); 6.98-7.11 (unresolved complex, 3H); 7.36-7.53 (unresolved complex, 4H); 7.56 (s, 1H); 8.58 (d, 1H); 12.27 (s, 1H). $[α]_D^{20}$=−138.6 (c=1/CH$_3$OH).

EXAMPLE 2

(2S)-N-(5-{2-[(cyclohexyloxy)methyl]phenyl}-1,3-thiazol-2-yl)-2-{[(2R)-2-3,5-difluorophenyl)-2-fluoroethanoyl]amino}propionamide (Compound No. 65) and (2S)-N-(5-{2-[(cyclohexyloxy)methyl]phenyl}-1,3-thiazol-2-yl)-2-{[(2S)-2-[3,5-difluorophenyl)-2-fluoroethanoyl]amino}propionamide (Compound No. 66)

EXAMPLE 2.1 methyl 3,5-difluoromandelate 2 ml of sulfuric acid at 95% by mass are added to 2 g of 3,5-difluoromandelic acid in solution in 25 ml of methanol, and the mixture is kept under reflux for 6 hours. The medium is concentrated, the residue is taken up in ethyl acetate and washed with a sodium hydroxide solution (0.1 N). The organic phase is dried over anhydrous sodium sulfate and 2 g of oil are obtained.

$^1$H NMR: δ in ppm (DMSO d6): 3.70 (s, 3H); 5.10 (s, 1H); 6.51 (s, 1H); 7.11-7.44 (unresolved complex, 3H).

EXAMPLE 2.2 methyl (3,5-difluorophenyl)fluoroacetate 2.3 g of N-ethyl-N-(trifluoro-λ$^4$-sulfanyl)-1-ethanamine are added dropwise at 20° C. to 2 g of methyl 3,5-difluoromandelate, obtained in step 2.1, in solution in 25 ml of dichloromethane, and the mixture is stirred for 18 hours at room temperature. The reaction medium is taken up in dichloromethane and washed with water, with a saturated aqueous sodium hydrogen carbonate solution, and then with a hydrochloric acid solution (0.5 N). The organic phase is dried over anhydrous sodium sulfate and concentrated to give 1.9 g of oil.

$^1$H NMR: δ in ppm (DMSO d6): 3.72 (s, 3H); 6.28 (d, 1H) 7.21-7.42 (unresolved complex, 3H).

EXAMPLE 2.3

(3,5-difluorophenyl)fluoroacetic acid 15 ml of a sodium hydroxide solution (1N) are added to 1.9 g of methyl (3,5-difluorophenyl)-fluoroacetate, obtained in step 2.2, in 60 ml of methanol and the mixture is stirred for 18 hours at room temperature. The medium is concentrated under vacuum, the residue is taken up in ethyl acetate and washed with an aqueous hydrochloric acid solution (0.5 M). The organic phase is dried over anhydrous sodium sulfate and concentrated to give 1.6 g of an orange-colored oil.

$^1$H NMR: δ in ppm (DMSO d6): 6.10 (d, 1H); 7.12-7.39 (unresolved complex, 3H).

EXAMPLE 2.4

(2S)-N-(5-{2-[(cyclohexyloxy)methyl]phenyl}-1,3-thiazol-2-yl)-2-{[(2R)-2-(3,5-difluorophenyl)-2-fluoroethanoyl]amino}propionamide and (2S)-N-(5-{2-[(cyclohexyloxy)methyl]phenyl}-1,3-thiazol-2-yl)-2-{[(2S)-2-(3,5-difluorophenyl)-2-fluoroethanoyl]amino}propionamide The procedure is carried out in the same manner as in step 1.8 of Example 1, replacing 3,5-difluorophenylacetic acid with (3,5-difluorophenyl)fluoroacetic acid, obtained in step 2.3. 0.5 g of the (SR) diastereoisomer and 0.5 g of the (SS) diastereoisomer are obtained.

Compound No. 65 (SR):

m.p.=78° C. $^1$H NMR: δ in ppm (DMSO d6): 1.19-1.88 (unresolved complex, 13H); 3.38 (m, 1H); 4.48 (s, 2H); 4.57 (q, 1H); 6.07 (d, 1H); 7.21-7.59 (unresolved complex, 8H); 8.96 (d, 1H); 12.36 (s, 1H). $[α]_D^{20}$=−115.4 (c=1/CH$_3$OH)

Compound No. 66 (SS):

m.p.=158° C. $^1$H NMR: δ in ppm (DMSO d6): 1.19-1.88 (unresolved complex, 13H); 3.34 (m, 1H); 4.49 (s, 2H); 4.57 (q, 1H); 6.09 (d, 1H); 7.21-7.62 (unresolved complex, 8H); 8.91 (d, 1H); 12.35 (s, 1H). $[α]_D^{20}$=−92 (c=1/CH$_3$OH)

EXAMPLE 3

(2S)-N-(5-{2-[(cyclohexyloxy)methyl]phenyl}-1,3-thiazol-2-yl)-2-{[(2R)-2-(3,5-difluorophenyl)-2-hydroxyethanoyl]amino}propionamide (Compound No. 50) and (2S)-N-(5-{2-[(cyclohexyloxy)methyl)phenyl}-1,3-thiazol-2-yl)-2-{[(2S)-2-[3,5-difluorophenyl)-2-hydroxyethanoyl]amino}propionamide (Compound No. 51)

1.8 g of benzotriazol-1-yloxytri-pyrrolidinophosphonium hexafluorophosphate and 0.45 ml of N-methylmorpholine are added at 0° C. to 0.5 g of 3,5-difluoromandelic acid in solution in 25 ml of dimethylformamide. After 20 min at 0° C., 0.9 g of (2S)-2-amino-N-(5-{2-[(cyclohexyloxy)methyl]

phenyl}-1,3-thiazol-2-yl)propionamide hydrochloride, obtained in step 1.7 of Example 1, is introduced and the mixture is stirred for 18 hours at 20° C. The reaction medium is poured over an aqueous sodium hydroxide solution (0.5 M) and extracted with ethyl acetate. The organic phase is dried over anhydrous sodium sulfate and concentrated. The residue is chromatographed on a silica column, eluting with a dichloromethane/methanol 99.5/0.5 (v/v) mixture and 0.22 g of (SS) diastereoisomer and 0.20 g of (SR) diastereoisomer are obtained.

Compound No. 50 (SR):
m.p.=169° C. $^1$H NMR: δ in ppm (DMSO d6): 1.18-1.47 (unresolved complex, 9H); 1.64 (m, 2H); 1.86 (m, 2H); 3.35 (m, 1H); 4.47 (s, 2H); 4.53 (m, 1H); 5.09 (m, 1H); 6.50 (d, 1H); 7.12-7.57 (unresolved complex, 8H); 8.35 (d, 1H); 12.28 (s, 1H). $[\alpha]_D^{20}$=−106 (c=1/CH$_3$OH)

Compound No. 51 (SS):
m.p.=159° C. $^1$H NMR: δ in ppm (DMSO d6): 1.19-1.48 (unresolved complex, 9H); 1.65 (m, 2H); 1.84 (m, 2H); 3.37 (m, 1H); 4.48 (s, 2H); 4.58 (m, 1H); 5.07 (m, 1H); 6.54 (d, 1H); 7.09-7.60 (unresolved complex, 8H); 8.59 (d, 1H); 12.25 (s, 1H). $[\alpha]_D^{20}$=−95 (c=1/CH$_3$OH)

EXAMPLE 4

(2S)-N-(5-{2-[(cyclohexyloxy)methyl)phenyl}-1,3-thiazol-2-yl)-2-{[2-(3,5-difluorophenyl)-2-oxoacetyl]amino}propionamide (Compound No. 61)

The procedure is carried out in the same manner as in step 1.8 of Example 1, replacing 3,5-difluorophenylacetic acid with (3,5-difluorophenyl)oxoacetic acid. 0.54 g of the compound is obtained. m.p.=78° C.

$^1$H NMR: δ in ppm (DMSO d6): 1.17-1.48 (unresolved complex, 9H); 1.63 (m, 2H); 1.82-1.86 (m, 2H); 3.36 (m, 1H); 4.48 (s, 2H); 4.71 (m, 1H); 7.34-7.74 (unresolved complex, 8H); 9.46 (d, 1H); 12.48 (s, 1H). $[\alpha]_D^{20}$=−122.9 (c=1/CH$_3$OH)

EXAMPLE 5

(2S)-N-(5-{2-[(cyclohexyloxy)methyl)phenyl}-1,3-thiazol-2-yl)-2-{[2-(3,5-difluorophenyl)propanoyl]-amino}pentanamide (Compound No. 58)

The procedure is carried out in the same manner as in step 1.8 of Example 1 by reacting (2S)-2-amino-N-(5-{2-[(cyclohexyloxy)methyl]phenyl}-1,3-thiazol-2-yl)pentanamide hydrochloride, obtained by a method similar to that described for the preparation of (2S)-2-amino-N-(5-{2-[(cyclohexyloxy)methyl]phenyl}-1,3-thiazol-2-yl)propionamide hydrochloride (steps 1.1 to 1.7 of Example 1), with 2-(3,5-difluorophenyl)propanoic acid. 0.52 g of the compound is obtained. m.p.=88° C.

$^1$H NMR: δ in ppm (DMSO d6): 0.82 (t, 3H); 1.18-1.91 (unresolved complex, 17H); 2.51 (m, 1H); 3.82 (q, 1H); 4.45 (s, 2H); 4.49 (m, 1H); 7.01-7.09 (unresolved complex, 3H); 7.36-7.64 (unresolved complex, 5H); 8.44 (d, 1H); 12.30 (s, 1H). $[\alpha]_D^{20}$=−78 (c=1/CH$_3$OH)

EXAMPLE 6

(2S)-2-{[2-(3,5-difluorophenyl)acetyl]-amino}-N-(5-{2-(isopropoxymethyl)-4-methoxyphenyl}-1,3-thiazol-2-yl)pentanamide (Compound No. 75)

EXAMPLE 6.1

2-bromo-5-methoxybenzol

2-Bromo-5-methoxybenzol is prepared from methyl 2-bromo-5-methoxybenzoate, which is commercially available, according to a method described by Stara, Irena G. et al., Tetrahedron, 54, 37, 1998, 11209-11234.

EXAMPLE 6.2

2-bromo-5-methoxybenzyl bromide

2-Bromo-5-methoxybenzyl bromide is prepared from 2-bromo-5-methoxybenzol, obtained in step 6.1, according to a method described by Fukuyama, Yoshiyasu et al., Heterocycles, 54, 1, 2001, 259-274.

EXAMPLE 6.3

(2S)-2-{[2-(3,5-difluorophenyl)-acetyl]amino}-N-(5-{2-(isopropoxymethyl)-4-methoxy-phenyl}-1,3-thiazol-2-yl)pentanamide (2S)-2-{[2-(3,5-Difluorophenyl)acetyl]amino}-N-(5-{2-(isopropoxymethyl)-4-methoxyphenyl}-1,3-thiazol-2-yl) pentanamide is prepared from 2-bromo-5-methoxybenzyl bromide, obtained in step 6.2, according to a method similar to that described in steps 1.1 to 1.8 of Example 1.

m.p.=73.9° C. $^1$H NMR: δ in ppm (DMSO d6): 0.87 (t, 3H); 1.12 (d, 6H); 1.26-1.40 (m, 2H); 1.60-1.72 (m, 2H); 3.52 (s, 2H); 3.58 (m, 1H); 3.72 (s, 3H); 4.41 (s, 2H); 4.51 (m, 1H); 6.92-7.34 (unresolved complex, 6H); 7.46 (s, 1H); 8.52 (d, 1H); 12.26 (s, 1H). $[\alpha]_D^{20}$=−121 (c=1/CH$_3$OH)

The following tables illustrate the chemical structures and the physical properties of a few of the compounds of the invention.

In these tables:
- m.p. (° C.) represents the melting point of the compound in degrees Celsius;
- $[\alpha_D]$ (c=1, CH$_3$OH) represents the optical rotation of the compound at the concentration of 1 g/l in methanol;
- (S) or (R) in columns "R$_3$" and "R$_5$, R$_5$," indicate the stereochemistry of the asymmetric carbons, carrying R$_3$ or R$_5$ respectively, in formula (I). For the carbon carrying R$_5$, the indication (S) or (R) does not relate to the case where R$_5$ and R$_5$' form together an oxo group.

The compounds described in this table are in the form of bases, except compound No. 68 which is in the form of a hexafluorophosphate salt. They were prepared according to the methods described above.

TABLE 1
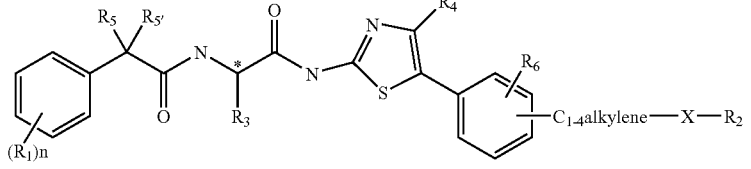
|No.|(R₁)n|R₃|R₄|R₅, R₅'| |m.p. (°C.)|[α_D] (c = 1, CH₃OH)|
|---|---|---|---|---|---|---|---|
|1.|3-F, 5-F|—CH₃ (RS)|H|H, H|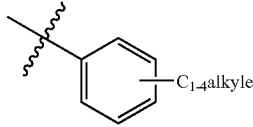|175|—|
|2.|3-F, 5-F|—CH₃ (RS)|H|H, H|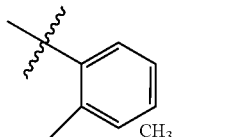|126|—|
|3.|3-F, 5-F|—CH₃ (RS)|H|H, H|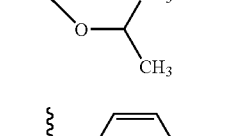|165|—|
|4.|3-F, 5-F|—CH₃ (RS)|H|H, H|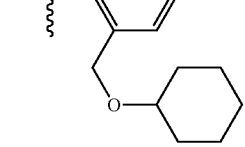|181|—|
|5.|3-F, 5-F|—CH₃ (RS)|H|H, H|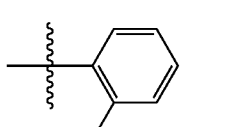|114|—|
|6.|3-F, 5-F|—CH₃ (RS)|H|H, H||147|—|

TABLE 1-continued
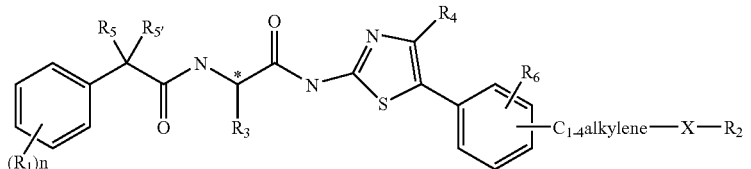
(I)
| No. | (R₁)n | R₃ | R₄ | R₅, R₅' | | m.p. (° C.) | [α_D] (c = 1, CH₃OH) |
|---|---|---|---|---|---|---|---|
| 7. | 3-F, 5-F | —CH₃ (RS) | H | H, H | 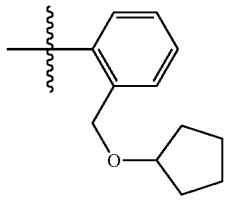 | 146 | — |
| 8. | 3-F, 5-F | —CH₃ (RS) | H | H, H | 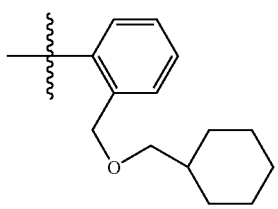 | 143 | — |
| 9. | 3-F, 5-F | —CH₂CH₃ (RS) | H | H, H | 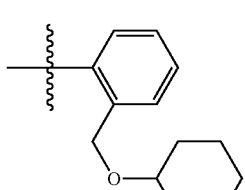 | 179 | — |
| 10. | 3-F, 5-F | —CH(CH₃)₂ (RS) | H | H, H | 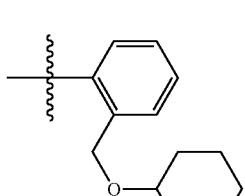 | 181 | — |
| 11. | n = 0 | —CH₃ (RS) | H | H, H | 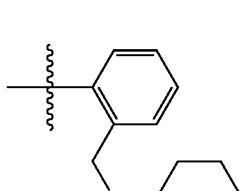 | 162 | — |

TABLE 1-continued (I)

| No. | (R₁)n | R₃ | R₄ | R₅, R₅' | (substituent structure) | m.p. (°C.) | [α_D] (c = 1, CH₃OH) |
|---|---|---|---|---|---|---|---|
| 12. | 3-F, 5-F | —CH₃ (RS) | —CH₃ | H, H | phenyl-CH₂-O-cyclohexyl (ortho) | 152 | — |
| 13. | 3-F, 5-F | —CH₃ (RS) | H | H, H | phenyl-CH₂-O-CH₃ (ortho) | 194 | — |
| 14. | 3-F, 5-F | —CH₃ (RS) | —CH₃ | H, H | phenyl-CH₂-O-cyclopentyl (ortho) | 104 | — |
| 15. | 3-F, 5-F | H | H | H, H | phenyl-CH₂-O-cyclohexyl (ortho) | 172 | — |
| 16. | 3-CH₃ | —CH₃ (S) | H | H, H | phenyl-CH₂-O-cyclohexyl (ortho) | 98 | −125 |
| 17. | 4-CH₃ | —CH₃ (S) | H | H, H | phenyl-CH₂-O-cyclohexyl (ortho) | 239 | −132 |

TABLE 1-continued
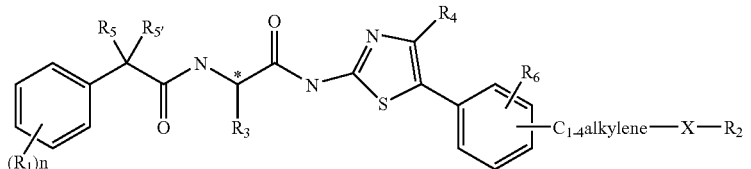
| No. | (R₁)n | R₃ | R₄ | R₅, R₅' | | m.p. (° C.) | [α_D] (c = 1, CH₃OH) |
|---|---|---|---|---|---|---|---|
| 18. | 3-Cl | —CH₃ (S) | H | H, H | 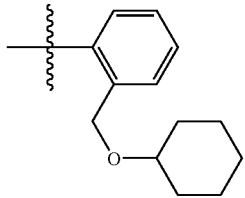 | 96 | −128 |
| 19. | 3-F | —CH₃ (S) | H | H, H | 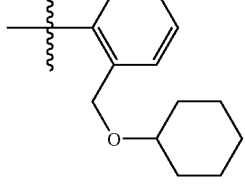 | 98 | −144 |
| 20. | 4-F | —CH₃ (S) | H | H, H | 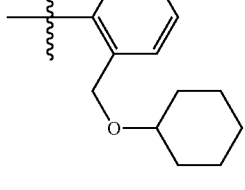 | 70 | −128 |
| 21. | 3-F, 5-F | —CH₃ (S) | H | H, H | 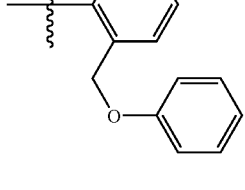 | 78 | −141 |
| 22. | 3-F, 5-F | —CH₃ (S) | H | H, H | 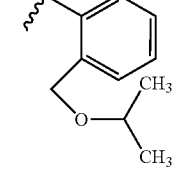 | 136 | −137 |

TABLE 1-continued (I)

| No. | (R₁)n | R₃ | R₄ | R₅, R₅' | R₆ | m.p. (° C.) | [α_D] (c = 1, CH₃OH) |
|-----|-------|-----|-----|---------|-----|------|------|
| 23. | 3-F, 5-F | —CH₃ (S) | —CH₃ | H, H | 2-(cyclohexyloxymethyl)phenyl | 85 | −52 |
| 24. | 3-F, 5-F | —CH₃ (S) | H | H, H | 3-(cyclohexyloxymethyl)phenyl | 123 | −190 |
| 25. | 3-F, 5-F | —CH₃ (R) | H | H, H | 2-(cyclohexyloxymethyl)phenyl | 95 | +135.8 |
| 26. | 3-F, 5-F | —CH₃ (S) | H | H, H | 2-(cyclohexyloxymethyl)phenyl | 140 | −138.6 |
| 27. | 3-F, 5-F | —CH₃ (S) | —CH₃ | H, H | 2-(isopropyloxymethyl)phenyl | 74 | −117.8 |
| 28. | 3-F, 5-F | —CH₃ (S) | —CH₃ | H, H | 2-(cyclopentyloxymethyl)phenyl | 141 | −93.5 |

TABLE 1-continued
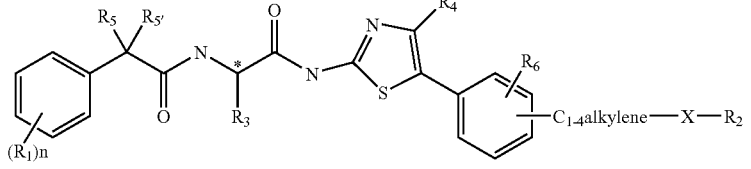
(I)
| No. | (R$_1$)n | R$_3$ | R$_4$ | R$_5$, R$_{5'}$ | | m.p. (° C.) | [α$_D$] (c = 1, CH$_3$OH) |
|---|---|---|---|---|---|---|---|
| 29. | 3,4(—O—CH$_2$—O—) | —CH$_3$ (S) | H | H, H | 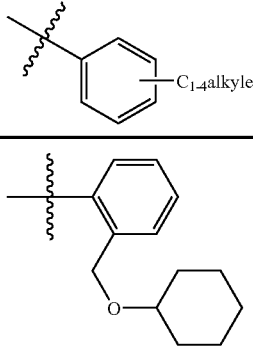 | 11 | −124 |
| 30. | 3-F, 4-F | —CH$_3$ (S) | H | H, H | 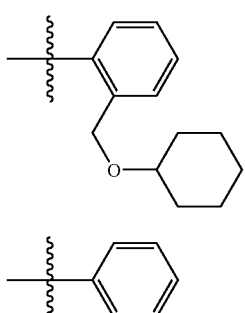 | 136 | −132 |
| 31. | 3-F, 5-F | —CH(CH$_3$)$_2$ (S) | H | H, H | 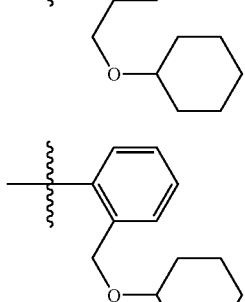 | 87 | −106 |
| 32. | 3-F, 5-F | —CH$_2$CH$_3$ (S) | H | H, H | 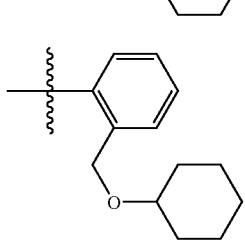 | 68 | −122 |
| 33. | 4-OCH$_3$ | —CH$_3$ (S) | H | H, H | 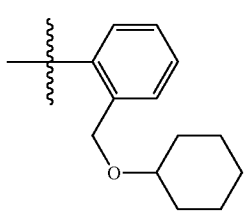 | 74 | −149 |
| 34. | 3-OCH$_3$ | —CH$_3$ (S) | H | H, H | | 94 | −139 |

TABLE 1-continued

Structure (I): Chemical structure with R groups as shown, including (R₁)n on phenyl, R₃ at chiral center, R₄ on thiazole, R₅ R₅', and R₆ with C₁₋₄alkylene—X—R₂ substituent.

| No. | (R₁)n | R₃ | R₄ | R₅, R₅' | [Ar-C₁₋₄alkylene-X-R₂ group] | m.p. (°C.) | [α_D] (c = 1, CH₃OH) |
|---|---|---|---|---|---|---|---|
| 35. | 3-OCH₃, 5-OCH₃ | —CH₃ (S) | H | H, H | 2-(cyclohexyloxymethyl)phenyl | 73 | −131 |
| 36. | 3-F, 5-F | —CH₂CH(CH₃)₂ (S) | H | H, H | 2-(cyclohexyloxymethyl)phenyl | 67 | −93 |
| 37. | 3-F, 5-F | —C(CH₃)₃ (S) | H | H, H | 2-(cyclohexyloxymethyl)phenyl | 73 | −107 |
| 38. | 4-Cl | —CH₃ (S) | H | H, H | 2-(cyclohexyloxymethyl)phenyl | 125 | −149.4 |
| 39. | 3-F, 5-F | —CH₃ (S) | H | H, H | 4-(cyclohexyloxymethyl)phenyl | 155 | −162 |
| 40. | 3-F, 5-F | —CH₃ (S) | H | H, H | 2-(isobutoxymethyl)phenyl | 161 | −139.1 |

TABLE 1-continued (I)

| No. | (R₁)n | R₃ | R₄ | R₅, R₅' | [R₆ structure] | m.p. (° C.) | [α_D] (c = 1, CH₃OH) |
|---|---|---|---|---|---|---|---|
| 41. | 3-F, 5-F | —CH₃ (S) | H | H, H | 2-(ethoxymethyl)phenyl | 173 | −149 |
| 42. | 3-F, 5-F | —(CH₂)₂CH₃ (S) | H | H, H | 2-(cyclohexyloxymethyl)phenyl | 134 | −102 |
| 43. | 3-F, 5-F | —CH₃ (S) | H | H, H | 3-(cyclohexylmethoxymethyl)phenyl | 144 | −165 |
| 44. | 3-F, 5-F | —CH₂-cyclohexyl (S) | H | H, H | 2-(cyclohexyloxymethyl)phenyl | 120 | −56 |
| 45. | 3-F, 5-F | —CH₃ (S) | H | H, H | 3-(isopropoxymethyl)phenyl | 136 | −121 |
| 46. | 3-F, 5-F | —CH₃ (S) | H | H, H | 4-(cyclohexylmethoxymethyl)phenyl | 166 | −166.6 |

TABLE 1-continued (I)

| No. | (R₁)n | R₃ | R₄ | R₅, R₅' | | m.p. (° C.) | [α_D] (c = 1, CH₃OH) |
|---|---|---|---|---|---|---|---|
| 47. | 3-F, 5-F | —(CH₂)₃CH₃ (S) | H | H, H | 2-(cyclohexyloxymethyl)phenyl | 77.6 | −84 |
| 48. | 3-OCF₃ | —CH₃ (S) | H | H, H | 2-(cyclohexyloxymethyl)phenyl | 60 | −119 |
| 49. | 3-F, 5-F | —CH₃ (S) | H | H, H | 2-(cyclopentyloxymethyl)phenyl | 236 | −140.3 |
| 50. | 3-F, 5-F | —CH₃ (S) | H | OH, H(R) | 2-(cyclohexyloxymethyl)phenyl | 169 | −106 |
| 51. | 3-F, 5-F | —CH₃ (S) | H | OH, H(S) | 2-(cyclohexyloxymethyl)phenyl | 159 | −95 |
| 52. | 3-F, 5-F | —(CH₂)₂CH₃ (S) | —CH₃ | H, H | 2-(cyclohexyloxymethyl)phenyl | 94 | −88.3 |

TABLE 1-continued
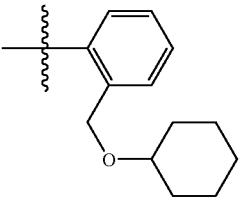
| No. | (R₁)n | R₃ | R₄ | R₅, R₅' | | m.p. (°C.) | [α_D] (c = 1, CH₃OH) |
|---|---|---|---|---|---|---|---|
| 53. | 3-F, 5-F | —(CH₂)₂CH₃ (S) | —CH₃ | OH, H(R) | 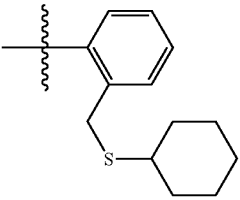 | 99.4 | −101.9 |
| 54. | 3-F, 5-F | —CH₃ (S) | H | H, H | | 91.6 | −116.5 |
| 55. | 3-F, 5-F | —(CH₂)₂CH₃ (S) | H | OH, H(S) | | 141 | −74.5 |
| 56. | 3-F, 5-F | —(CH₂)₂CH₃ (S) | H | OH, H(R) | | 112 | −64.2 |
| 57. | 3-F, 5-F | —(CH₂)₂CH₃ (S) | —CH₃ | OH, H(S) | | 115 | −63.2 |

TABLE 1-continued (I)

| No. | (R₁)n | R₃ | R₄ | R₅, R₅' | [structure column] | m.p. (°C.) | [α_D] (c = 1, CH₃OH) |
|---|---|---|---|---|---|---|---|
| 58. | 3-F, 5-F | —(CH₂)₂CH₃ (S) | H | CH₃, H | benzyl-O-cyclohexyl | 88 | −78 |
| 59. | 3-F, 5-F | —(CH₂)₂CH₃ (S) | —CH₂CH₃ | H, H | benzyl-O-cyclohexyl | 80 | −94.9 |
| 60. | 3-F, 5-F | —(CH₂)₂CH₃ (S) | H | =O | benzyl-O-cyclohexyl | 77 | −94.5 |
| 61. | 3-F, 5-F | —CH₃ (S) | H | =O | benzyl-O-cyclohexyl | 78 | −122.9 |
| 62. | 3-F, 5-F | —CH₃ (S) | —CH₂CH₃ | H, H | benzyl-O-cyclohexyl | 70 | −118 |
| 63. | 3-F, 5-F | —(CH₂)₂CH₃ (S) | CH(CH₃)₂ | H, H | benzyl-O-cyclohexyl | 74 | −81.6 |

TABLE 1-continued
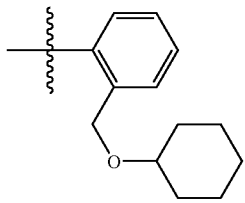
(I)
| No. | (R$_1$)n | R$_3$ | R$_4$ | R$_5$, R$_5'$ | | m.p. (° C.) | [α$_D$] (c = 1, CH$_3$OH) |
|---|---|---|---|---|---|---|---|
| 64. | 3-F, 5-F | —(CH$_2$)$_2$CH$_3$ (S) | H | F, H | 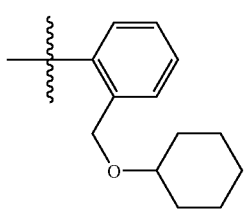 | 139 | −109 |
| 65. | 3-F, 5-F | —CH$_3$ (S) | H | F, H(R) | 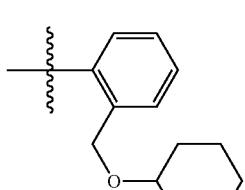 | 78 | −115.4 |
| 66. | 3-F, 5-F | —CH$_3$ (S) | H | F, H(S) | 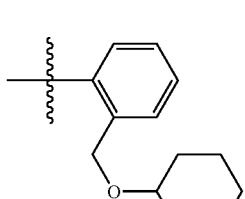 | 158 | −92 |
| 67. | 3-F, 5-F | —(CH$_2$)$_2$CH$_3$ (S) | H | F, H | 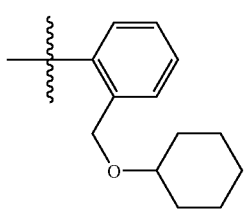 | 91 | −91 |
| 68. | 3-F, 5-F | —(CH$_2$)$_2$CH$_3$ (S) | —CH$_3$ | H, H | 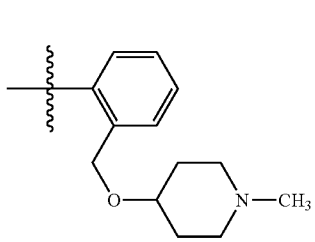 | 186 | −51.6 |

TABLE 1-continued (I)

| No. | (R₁)n | R₃ | R₄ | R₅, R₅' | | m.p. (°C.) | [α_D] (c = 1, CH₃OH) |
|---|---|---|---|---|---|---|---|
| 69. | 3-F, 5-F | —CH₂CH₃ (S) | —CH₃ | H, H | 2-(isopropoxymethyl)phenyl | 79 | −107.8 |
| 70. | 3-F, 5-F | —CH₂CH₃ (S) | H | H, H | 2-(isopropoxymethyl)phenyl | 73 | −119.8 |
| 71. | 3-F, 5-F | —(CH₂)₂CH₃ (S) | —CH₃ | H, H | 2-(isopropoxymethyl)phenyl | 66.6 | −93.5 |
| 72. | 3-F, 5-F | —(CH₂)₂CH₃ (S) | H | H, H | 2-(isopropoxymethyl)phenyl | 74 | −114 |
| 73. | 3-F, 5-F | —CH₃ (S) | H | H, H | 2-((4-methoxycyclohexyloxy)methyl)phenyl | 149 | −115 |

TABLE 1-continued

| No. | (R₁)n | R₃ | R₄ | R₅, R₅' | [structure] | m.p. (°C.) | [α_D] (c = 1, CH₃OH) |
|---|---|---|---|---|---|---|---|
| 74. | 3-F, 5-F | —(CH₂)₂CH₃ (S) | H | F, F | [2-(cyclohexyloxymethyl)phenyl] | 68 | −66.2 |
| 75. | 3-F, 5-F | —(CH₂)₂CH₃ (S) | H | H, H | [2-(isopropoxymethyl)-4-methoxyphenyl] | 73.9 | −121 |

The compounds of the invention have been the subject of pharmacological trials which have shown their value as active substances in therapy.

They have in particular been tested for their β-amyloid peptide (β-A4) production inhibiting effects.

β-Amyloid peptide (β-A4) is a fragment of a larger precursor protein called APP (amyloid precursor protein). The latter is produced and is present in various cells of animal or human tissue. At the cerebral level, its cleavage by protease-type enzymes leads to the formation of the β-A4 peptide which accumulates in the form of an amyloid plaque. The two proteases responsible for the production of the amyloid peptide are known by the name of beta- and gamma-secretases (Wolfe M S, Secretase targets for Alzheimer's disease: identification and therapeutic potential, J. Med. Chem., Jun. 21, 2001; 44(13), 2039-60).

However, it has been demonstrated that this gradual deposition of the β-A4 peptide is neurotoxic and could play an important role in Alzheimer's disease.

Thus, the compounds of the present invention, as inhibitor of the production of β-amyloid peptide (β-A4) by inhibition of gamma-protease, can be used in the treatment of pathologies such as senile dementia, Alzheimer's disease, Down's syndrome, Parkinson's disease, amyloid angiopathy and/or cerebrovascular disorders.

The tests were carried out according to the protocol described below.

For the β-amyloid cellular trial, the CHO-K1 line coexpressing the CT100 of APP and PS1 M146L clone 30-12 is used. The line targets the inhibition of gamma-secretase. Presenilin is linked to the gamma-secretase activity (Wolfe M S, Haass C., The Role of presenilins in gamma-secretase activity, J. Biol. Chem., Feb. 23, 2001, 276(8), 5413-6) and its coexpression with the amyloid protein or its N-terminal fragment causes an increase in the secretion of the A1-42 peptide (β-A4) thus generating a pharmacological tool which makes it possible to evaluate inhibition by the compounds of formula (I) of the production of the β-A4 peptide. The inoculation of the 96-well culture plates is carried out at the rate of 1×10⁵ cells per well in 150 μl of incubation medium. The presence of a minimum percentage (1.3% final) of serum allows cellular adhesion to the plastic after 2-3 hours of incubation at 37° C., in the presence of 5% CO₂. The products (15 μl) are tested at 10 μM DMSO 1% final and are incubated for 24-25 h at 37° C. in the presence of 5% CO₂ and of 100% humidity. After this incubation of 24-25 h, the cellular supernatants (100 μl) are transferred to the ELISA plates, treated with the capture antibody 6E10 (6E10, epitope: aa1-17, INTERCHIM/SENETEK 320-10), to determine the amount of amyloid peptides secreted by the cells in the presence of compounds of the invention. A series for a synthetic control peptide, "peptide 1-40", at 5 and 10 ng/ml is treated in parallel. The ELISA plates are incubated overnight at 4° C.

The quantity of bound peptide is detected in an indirect manner in the presence of a competitor corresponding to the truncated peptide, peptide 1-28 coupled to biotin which is then detected with streptavidin coupled to alkaline phosphatase. The substrate, p-Nitrophenyl Phosphate (pNPP FAST p-Nitrophenyl Phosphate, Sigma N2770), gives a yellow soluble reaction product which can be read at 405 nm. The reaction is stopped with a 0.1M EDTA solution. For that, after attachment of the amyloid peptide in the ELISA plate, 50 μl of biotinylated peptide 1-28 are added to 100 μl of cell supernatant and incubated for 30 minutes at room temperature. The ELISA plates are then washed 3 times. After drying by inverting on absorbent paper, 100 μl of streptavidin-Alkaline Phosphatase (Interchim/Jackson ImmunoResearch Laboratories 016-050-084), are added per well and incubated for 1 hour at room temperature. The plates are again washed and then alkaline phosphatase substrate (pNPP 1 mg/ml) is added in an amount of 100 μl per well. After incubating for 30 minutes at room temperature, the reaction is stopped by the addition of 100 μl per well of 0.1M EDTA and the reading is carried out at 405 nm.

The compounds of formula (I) of the invention showed an IC50 (50% inhibitory concentration) of less than 500 nM, more particularly of less than 100 nM.

The results of the biological tests show that the compounds are inhibitors of the formation of the β-amyloid peptide (β-A4).

Thus, these compounds may be used in the treatment of pathologies in which an inhibitor of the formation of the β-amyloid peptide (β-A4) provides a therapeutic benefit. In particular, such pathologies are senile dementia, Alzheimer's disease, Down's syndrome, Parkinson's disease, amyloid angiopathy and cerebrovascular disorders.

The use of the compounds of the invention for the preparation of a medicament for treating the abovementioned pathologies forms an integral part of the invention.

The subject of the invention is also medicaments which comprise a compound of formula (I), or an addition salt thereof with a pharmaceutically acceptable acid or alternatively a hydrate or a solvate of the compound of formula (I). These medicaments find their use in therapy, in particular in the treatment of the abovementioned pathologies.

According to another of its aspects, the present invention relates to pharmaceutical compositions containing, as active ingredient, at least one compound of the invention. These pharmaceutical compositions contain an effective dose of a compound of the invention, or a pharmaceutically acceptable salt, a hydrate or a solvate of the said compound, and optionally one or more pharmaceutically acceptable excipients.

The said excipients are chosen, according to the pharmaceutical dosage form and the desired mode of administration, from the usual excipients which are known to persons skilled in the art.

In the pharmaceutical compositions of the present invention for oral, sublingual, subcutaneous, intramuscular, intravenous, topical, local, intratracheal, intranasal, transdermal or rectal administration, the active ingredient of formula (I) above, or its optional salt, solvate or hydrate, may be administered in unit form for administration, as a mixture with conventional pharmaceutical excipients, to animals and to human beings for the prophylaxis or the treatment of the above disorders or diseases.

The appropriate unit forms for administration comprise the forms for oral administration such as tablets, soft or hard gelatine capsules, powders, granules, chewing gums and oral solutions or suspensions, the forms for sublingual, buccal, intratracheal, intraocular or intranasal administration or for administration by inhalation, the forms for subcutaneous, intramuscular or intravenous administration and the forms for rectal or vaginal administration. For topical application, the compounds of the invention may be used in creams, ointments or lotions.

For example, when a solid composition in the form of tablets is prepared, the main active ingredient is mixed with a pharmaceutical excipient, such as gelatine, starch, lactose, magnesium stearate, talc, gum arabic and the like. The tablets may be coated with sucrose, a cellulosic derivative, or other substances. The tablets may be produced by various techniques, direct compression, dry granulation, wet granulation or hot-melt.

To obtain the desired prophylactic or therapeutic effect, the dose of active ingredient may vary between 0.1 mg and 200 mg per kg of bodyweight and per day. Although these dosages are examples of an average situation, there may be specific cases where higher or lower dosages are appropriate, such dosages also belong to the invention. According to the usual practice, the dosage appropriate for each patient is determined by the doctor according to the mode of administration, the weight and the response of the said patient.

Each unit dose may contain from 0.1 to 1000 mg, preferably from 0.1 to 500 mg, of active ingredient in combination with one or more pharmaceutical excipients. This unit dose may be administered 1 to 5 times per day so as to administer a daily dosage of 0.5 to 5000 mg, preferably of 0.5 to 2500 mg.

The present invention according to another of its aspects also relates to a method for treating the pathologies indicated above which comprises the administration of a compound of the invention, of a pharmaceutically acceptable salt, of a solvate or of a hydrate of the said compound.

The invention claimed is:

1. A compound corresponding to the general formula (I):

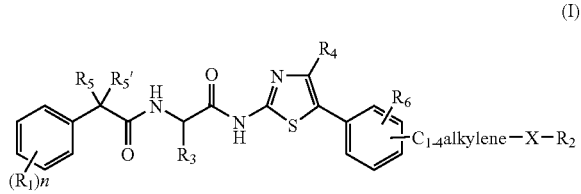

(I)

in which, n is equal to 0, 1, 2 or 3;

X represents an oxygen or sulfur atom;

$R_1$ represents, independently of each other when n=2 or 3, a halogen atom, a hydroxyl, a $C_{1-3}$ alkyl, a $C_{1-3}$ alkoxy, a trifluoromethyl, a trifluoromethyloxy or a methylenedioxy;

$R_2$ represents a $C_{1-6}$ alkyl group optionally substituted with a $C_{3-7}$ cycloalkyl group, a phenyl, a $C_{1-3}$ alkoxy group, a hydroxyl or a halogen atom; a $C_{3-7}$ cycloalkyl, piperidinyl or phenyl group; the $C_{3-7}$ cycloalkyl, piperidinyl and phenyl groups being optionally substituted with one or more $C_{1-3}$ alkyl groups, $C_{1-3}$ alkoxy groups, a hydroxyl or a halogen atom;

$R_3$ represents a hydrogen atom or a $C_{1-6}$ alkyl group optionally substituted with a $C_{3-7}$ cycloalkyl group;

$R_4$ represents a hydrogen atom or a $C_{1-4}$ alkyl group;

$R_5$ and $R_{5'}$ represent, independently of each other, a hydrogen atom, a hydroxyl, a halogen atom, or a $C_{1-3}$ alkyl group; or $R_5$ and $R_{5'}$ form together an oxo group; and $R_6$ represents a hydrogen atom, a halogen atom, a $C_{1-3}$ alkyl, a $C_{1-3}$ alkoxy, a trifluoromethyl or a trifluoromethoxy; or said compound in the form of a base, an addition salt with an acid, a hydrate or a solvate.

2. The compound according to claim 1 wherein:

X represents an oxygen or sulphur atom;

$R_1$ represents, independently of each other when n=2 or 3, a halogen atom, a methylenedioxy, a $C_{1-3}$ alkyl group, a $C_{1-3}$ alkoxy group or a trifluoromethyloxy;

$R_2$ represents a $C_{1-4}$ alkyl group optionally substituted with a $C_{4-7}$ cycloalkyl or phenyl group; a $C_{4-7}$ cycloalkyl, piperidinyl or phenyl group; the $C_{4-7}$ cycloalkyl, piperidinyl and phenyl groups being optionally substituted with one or more $C_{1-3}$ alkyl or $C_{1-3}$ alkoxy groups;

$R_3$ represents a hydrogen atom or a $C_{1-4}$ alkyl group, optionally substituted with a $C_{4-7}$ cycloalkyl group;

$R_4$ represents a hydrogen atom or a $C_{1-3}$ alkyl group;

$R_5$ and $R_{5'}$ represent, independently of each other, a hydrogen or halogen atom, a hydroxyl or a $C_{1-3}$ alkyl group; or $R_5$ and $R_{5'}$ form together an oxo group; and $R_6$ represents a hydrogen atom or a $C_{1-3}$ alkoxy; or said compound in the form of a base, an addition salt with an acid, a hydrate or a solvate.

3. The compound of formula (I) according to claim 1 wherein:

X represents an oxygen atom;

$R_1$ represents, independently of each other when n=2 or 3, a halogen atom;

$R_2$ represents a $C_{1-4}$ alkyl group optionally substituted with a $C_{4-7}$ cycloalkyl or phenyl group; a $C_{4-7}$ cycloalkyl, piperidinyl or phenyl group;

the $C_{4-7}$ cycloalkyl, piperidinyl and phenyl groups being optionally substituted with 1 or 2 $C_{1-3}$ alkyl or $C_{1-3}$ alkoxy groups;

$R_3$ represents a methyl, ethyl or propyl;

$R_4$ represents a hydrogen atom or a methyl;

$R_5$ and $R_{5'}$ represent, independently of each other, a hydrogen or fluorine atom, a hydroxyl or a methyl; or $R_5$ and $R_{5'}$ form together an oxo group; and $R_6$ represents a hydrogen atom or a methoxy; or said compound in the form of a base, an addition salt with an acid, a hydrate or a solvate.

4. A method for preparing a compound of formula (I) according to claim 1 wherein:

a peptide coupling of the compound of formula (VII)

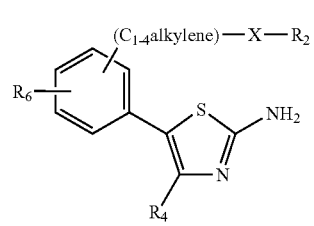

(VII)

with the amino acid of formula (VIII)

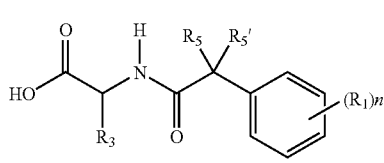

(VIII)

in which n, X, $R_1$, $R_2$, $R_3$, $R_4$, $R_5$ and $R_{5'}$ are as defined in formula (I) according to claim 1, is carried out.

5. A method for preparing a compound of formula (I) according to claim 1 in which $R_3$ does not represent a hydrogen atom, by peptide coupling of an amine of formula (XIII)

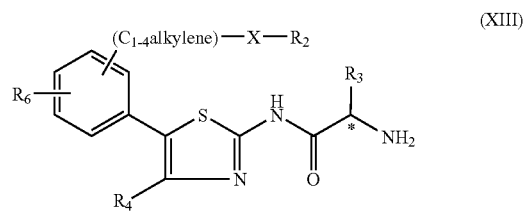

(XIII)

with an acid of formula (XIV)

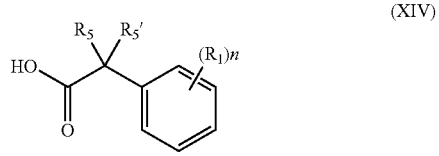

(XIV)

in which n, X, $R_1$, $R_2$, $R_3$, $R_4$, $R_5$ and $R_{5'}$ are as defined in formula (I) according to claim 1.

6. A pharmaceutical composition containing at least one compound of formula (I) according to claim 1 in the form of a pharmaceutically acceptable base, salt, hydrate or solvate and optionally one or more pharmaceutically acceptable excipients.

7. A method for preparing a compound of formula (I) according to claim 2 wherein:

a peptide coupling of the compound of formula (VII)

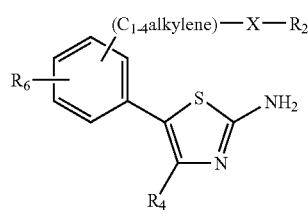

(VII)

with the amino acid of formula (VIII)

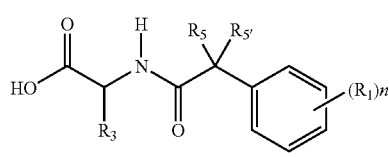

(VIII)

in which n, X, $R_1$, $R_9$, $R_3$, $R_4$, $R_5$ and $R_{5'}$ are as defined in formula (I) according to claim 2, is carried out.

8. A method for preparing a compound of formula (I) according to claim 3 wherein:

a peptide coupling of the compound of formula (VII)

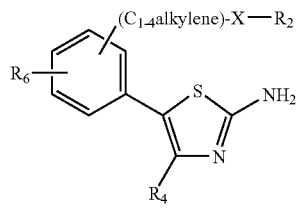
(VII)

with the amino acid of formula (VIII)

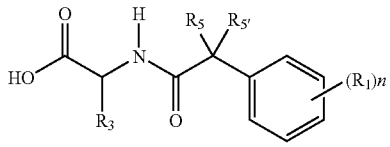
(VIII)

in which n, X, $R_1$, $R_2$, $R_3$, $R_4$, $R_5$ and $R_{5'}$ are as defined in formula (I) according to claim 2, is carried out.

9. A method for preparing a compound of formula (I) according to claim 2 in which $R_3$ does not represent a hydrogen atom, by peptide coupling of an amine of formula (XIII)

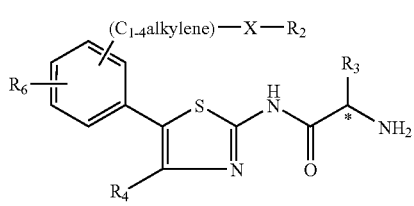
(XIII)

with an acid of formula (XIV)

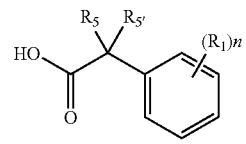
(XIV)

in which n, X, $R_1$, $R_9$, $R_3$, $R_4$, $R_5$ and $R_{5'}$ are as defined in formula (I) according to claim 2.

10. A method for preparing a compound of formula (I) according to claim 3 in which $R_3$ does not represent a hydrogen atom, by peptide coupling of an amine of formula (XIII)

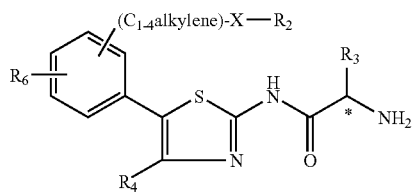
(XIII)

with an acid of formula (XIV)

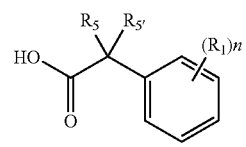
(XIV)

in which n, X, $R_1$, $R_2$, $R_3$, $R_4$, $R_5$ and $R_{5'}$ are as defined in formula (I) according to claim 2.

11. A pharmaceutical composition containing at least one compound of formula (I) according to claim 2 in the form of a pharmaceutically acceptable base, salt, hydrate or solvate and optionally one or more pharmaceutically acceptable excipients.

12. A pharmaceutical composition containing at least one compound of formula (I) according to claim 3 in the form of a pharmaceutically acceptable base, salt, hydrate or solvate and optionally one or more pharmaceutically acceptable excipients.

* * * * *